United States Patent
Wonn

[11] 4,009,616
[45] Mar. 1, 1977

[54] ACOUSTIC METHOD FOR MEASURING GAS PRESSURE

[75] Inventor: James W. Wonn, Irwin, Pa.

[73] Assignee: Westinghouse Electric Corporation, Pittsburgh, Pa.

[22] Filed: Jan. 29, 1975

[21] Appl. No.: 545,238

[52] U.S. Cl. .................. 73/398 R; 73/67.5 R; 176/19 LD
[51] Int. Cl.² .................. G01L 9/00; G01N 29/02
[58] Field of Search .......... 73/24, 398, 67.5 R, 73/556, 557, 561

[56] References Cited

UNITED STATES PATENTS

| | | | |
|---|---|---|---|
| 2,527,208 | 10/1950 | Berry et al. | 73/398 |
| 2,938,386 | 5/1960 | Anderson et al. | 73/398 |
| 3,019,656 | 2/1962 | Millar | 73/398 |
| 3,204,458 | 9/1965 | Gillen | 73/194 |
| 3,350,271 | 10/1967 | Maidment | 176/19 |
| 3,357,243 | 12/1967 | Woodcock | 73/194 |
| 3,823,068 | 7/1974 | Worlton et al. | 176/19 X |

FOREIGN PATENTS OR APPLICATIONS 739,181  7/1966  Canada .................. 73/398

Primary Examiner—Herbert Goldstein
Attorney, Agent, or Firm—D. C. Abeles

[57] ABSTRACT

A non-destructive acoustic method for measuring gas pressure in a hermetically sealed enclosure. In accordance with the method, an acoustic signal is generated and transmitted through the gas medium within the enclosure. The acoustic impedance mismatch between the enclosure and the gas medium is dependent upon the pressure of the gas and correspondingly affects the transmissivity of the acoustic signal. The signal is received after traversing a given travel path through the gas and converted into a corresponding electrical output calibrated against a standard to provide a direct measure of the pressure of the gas within the enclosure. In the preferred arrangement, the enclosure is acoustically damped to substantially dissipate acoustic energy traveling within the enclosure walls.

8 Claims, 3 Drawing Figures

ACOUSTIC METHOD FOR MEASURING GAS PRESSURE

BACKGROUND OF THE INVENTION

This invention pertains to non-destructive acoustic monitoring methods and more specifically to such methods that can be employed to monitor the gas pressure within a hermetically sealed enclosure.

A number of articles of manufacture contain a presurized gas as part of their operative embodiment. For example, as is well known in the art, a number of fuel elements for nuclear reactors are pressurized during manufacture to provide support for the fuel element cladding during operation under irradiation and external coolant pressure. To assure the quality of the manufactured items as well as the integrity of such items during periods of storage it is desirable to employ non-destructive testing techniques to measure the internal pressure of such items before application in their intended environment.

Methods of non-destructively measuring pressure are particularly important in the manufacture of nuclear fuel elements because of the adverse effects associated with fuel element failures during reactor operation. Testing methods presently under consideration call for destructively testing a sampling of fuel elements in each manufacturing lot, or implanting special pressure indicating devices in or on randomly selected elements. In either case, such methods rely on statistical data which may well prove unreliable. In addition, the industry is presently experimenting with a method that requires dipping of the plenum end of the fuel element into a liquid nitrogen bath to locally chill the gas in the plenum and cause a decrease in the internal gas pressure. The decrease in pressure apparently produces changes in the overall dimension of the element which can be related to the internal pressure. Aside from the question of accuracy, serious problems are encountered by subjecting various critical weldments on the fuel element to extreme thermal transients as anticipated by this experimental method.

Accordingly, a new method is desired capable of non-destructively measuring gas pressure within a hermetically sealed enclosure.

SUMMARY OF THE INVENTION

Briefly, this invention overcomes the difficulties of the prior art by providing a method for acoustically monitoring, non-destructively, the gas pressure within a hermetically sealed enclosure. In accordance with the method of this invention an acoustic signal is transmitted into and through the walls of the enclosure along a path through the gas medium. The transmitted signal is received after it has traveled a given path through the gas medium and converted to a corresponding electrical output which is calibrated as a direct measure of the pressure of the gas. In the preferred arrangement the enclosure is damped to substantially dissipate acoustic energy traveling within its walls. In this way, the effective acoustic path is almost entirely directed through the gas medium.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

Figure 1:
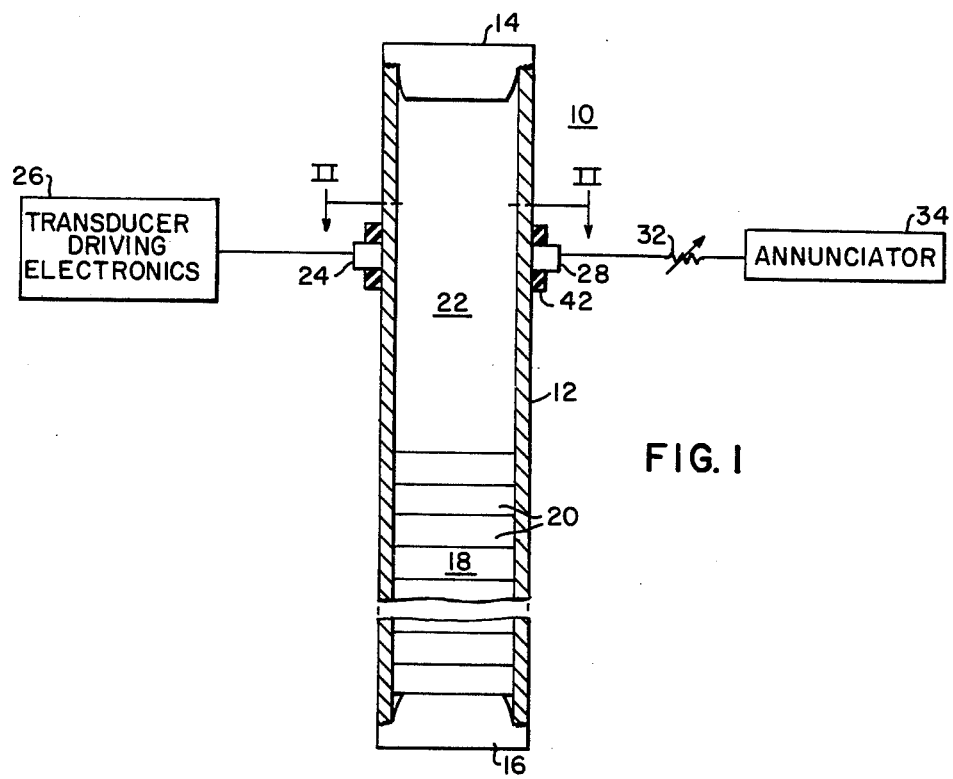
FIG. 1 is a schematic representation of the method of this invention as applied to measuring the internal gas pressure of a nuclear fuel element.
Figure 2:
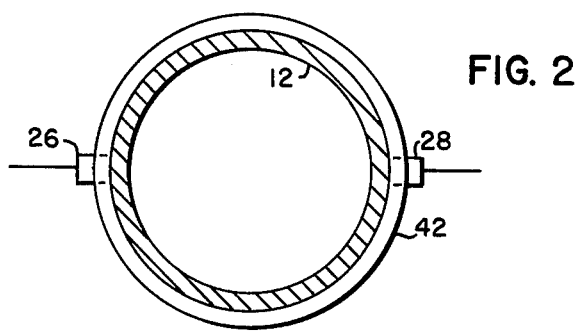
FIG. 2 is a cross-section of FIG. 1 taken along the lines II—II thereof.

FIG. 1 illustrates one example of apparatus which can be employed in practicing the method of this invention applied to a cylindrical tubular enclosure confining a pressurized gas. More specifically, a nuclear fuel element 10 is illustrated having an elongated thin walled tubular cladding 12 hermetically sealed at each end by a pair of end plugs 14 and 16. The hollow interior portion of the cladding houses a fuel region 18 having a tandem array of nuclear pellets 20, and a gas plenum 22 which is normally pressurized with helium to approximately 30 atmospheres.

In accordance with this invention an acoustic transducer 24, energized by the driving electronics 26, generates an acoustic signal, preferably in the sonic to ultrasonic range, which is transmitted through the cladding wall 12, diametrically across the gas plenum 22 and through the opposite cladding wall where it is received by a second acoustic transducer 28. The transducer 28 provides a corresponding electrical signal, which when calibrated as schematically represented by the variable resistor 32, will provide an output which is directly proportional to the internal pressure within the plenum as can be appreciated from the following analytical explantion.

The speed of sound in a gas, $C_{gas}$ can be represented by, $$C_{gas} = \left(\frac{\gamma P_o}{\rho_{gas}}\right)^{1/2}$$

where
$P_o$ = static pressure; and
$\gamma$ = ratio of specific heats

Similarly, the density of an ideal gas ($\rho$) is directly proportional to the absolute pressure, P, and can be represented by the equation, $$\rho_{gas} = KP_o$$

where $K$ is the proportionality constant.

The acoustic impedance, Z, of a gas can be given by, $$Z_{gas} = \rho_{gas} C_{gas}.$$

Substituting equations 1 and 2 into equation 3 for the impedance expression:

$$Z_{gas} = KP_o \left(\frac{\gamma P_o}{KP_o}\right)^{1/2} = P_o (k\tau)^{1/2}$$

Thus, the acoustic impedance of the gas is directly proportional to the gas pressure.

The speed of sound in a metal can similarly be given by, $$C_{metal} = \left(\frac{Y}{\rho_{metal}}\right)^{1/2}$$

where
$Y$ = Young's modulus and
$\rho$ metal = metal density.
The acoustic impedance of the metal can be represented by, $$Z_{metal} = \rho_{metal} \cdot C_{metal}$$

Since both Young's modulus and density are essentially pressue invariant for metals, $Z_{metal}$ is independent of applied pressure.

In order to understand the operation of the method of this invention it is necessary to calculate the intensity transmission coefficient for ultrasound going through one metal wall into a gas volume and through the opposite metal wall. The transmission intensity coefficients at the respective interfaces can be correspondingly represented by $\alpha_1$ and $\alpha_2$, where:

$$\alpha_1 = \frac{I_{2+}}{I_{1+}} \tag{7}$$

and;

$$\alpha_2 = \frac{I_{3+}}{I_{2+}}; \tag{8}$$

where $I_{1+}$, $I_{2+}$ and $I_{3+}$ are the acoustic intensities in the forward direction for the metal, gas, metal mediums respectively along the path of travel of the acoustic signal. The composite transmission coefficient going from metal to gas to metal, can be represented by, $$\alpha_{13} = \frac{I_{3+}}{I_{1+}} \tag{9}$$

Equation 9 can be expanded employing equations 7 and 8 as follows:

$$\alpha_{13} = \frac{I_{3+}}{I_{1+}} = \frac{I_{3+}}{I_{2+}} \cdot \frac{I_{2+}}{I_{1+}} = \alpha_1 \cdot \alpha_2 \tag{10}$$

The transmission intensity coefficients can then be expressed in terms of the interface impedance ratios $r$ as follows:

$$\alpha_1 = \frac{4r_1}{(r_1 + 1)^2} \tag{11}$$

and $$\alpha_2 = \frac{4r_2}{(r_2 + 1)^2} \tag{12}$$

where $$r_1 = \frac{Z_{gas}}{Z_{metal}} \text{ and } r_2 = \frac{Z_{metal}}{Z_{gas}}. \tag{13}$$

Using typical values for the impedances of metals and gasses, $r_1$ equals approximately $10^{-6}$ and $r_2$ equals approximately $10^{+6}$. For such extreme values of $r$, equations 11 and 12 can be approximated as:

$$\alpha_1 = 4r_1 \tag{14}$$

and $$\alpha_2 = 4/r_2. \tag{15}$$

The composite transmission coefficient can then be calculated employing the equations 14 and 15 and equation 10 to obtain:

$$\alpha_{13} = \alpha_1 \cdot 2 \cdot = 4r_1 \cdot (4/r_2) \tag{16}$$

From equation 13, $(1/r_2) = r_1$ so that $$\alpha_{13} = (4r_1)^2 \tag{17}$$

Inasmuch as $Z_{gas}$ is proportional to pressure and $Z_{metal}$ is constant the composite intensity transmission coefficient can be expressed as a function of the internal pressure, P:

$$\alpha_{13}(P) = (K'Pr_1)^2; \tag{18}$$

Where $K'$ is a proportionality constant.

Thus, the transmitted ultrasonic intensity is proportional to the square of the internal gas pressure.

As an example, the following equation is set forth to illustrate the ratio of the transmitted acoustic intensities for a fully pressurized verus a completely depressurized fuel element;

$$\frac{\alpha_{13}(30 \text{ atm})}{\alpha_{13}(1 \text{ atm})} = \left(\frac{K' \cdot 30 \cdot r_1}{K' \cdot r_1}\right)^2 = (30)^2 = 900 \tag{19}$$

Figure 3:
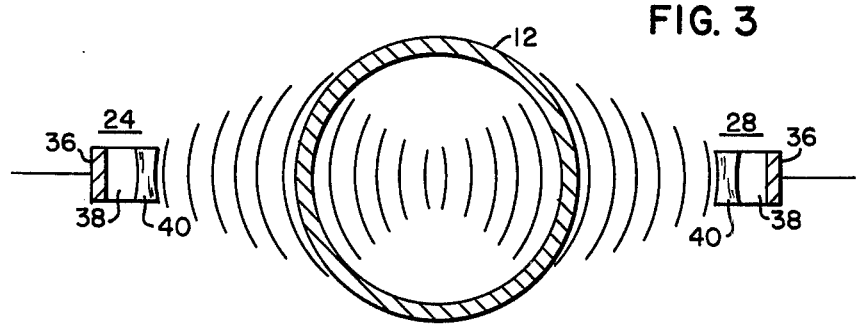
FIG. 3 is a schematic representation of the transducer and wave fronts employed in the particular application to cylindrical enclosures.

The above calculations assume that plane acoustic waves are employed at normal incidence. However, the same results can apply to cylindrical coordinates, such are encountered in the fuel element illustrated in the preferred embodiment, if cylindrical ultrasonic waves concentric with the axis of the cladding are employed. FIG. 3 illustrates an arrangement for obtaining cylindrical waves to be applied in this type of configuration. Essentially, the transducers 24 and 28 are identical and include a piezoelectric generating element 36 which is electrically excited by an electronic driving circuit to emit an acoustic wave. The transmitted signal is conducted through an acoustically conductive medium 38 such as water and focused into the desired form by the lens 40. The path of travel of the acoustic signal into and out of the cladding 12 is terminated at the receiving transducer 28 which converts the received signal into a corresponding electrical output. Desirably, the transmitted signal is provided in pulsed form to maximize the signal to noise ratio.

In the preferred form of practicing the method of this invention the enclosure is acoustically damped, as represented by the damping material 42 provided around the cladding 12, to substantially dissipate the acoustic energy transmitted circumferentially around the cladding. This improvement effectively directs the acoustic signal through the gas medium to the receiving transducer. The damping material 42 can be any one of a number of known acoustic damping materials such as are employed in state of the art transducers to affect ring down.

Thus, this invention provides a technique for rapidly measuring the pressure of a gas contained within a hermetically sealed enclosure without destroying the integrity of the container. Accordingly, the method provides a convenient tool for assuring the quality of articles of manufacture as well as items that have been stored for extended periods of time.

I claim as my invention:

1. A method of nondestructively measuring over a wide continuous range of pressures the gas pressure within a pressurized nuclear fuel element having a nuclear fuel region and a gas plenum hermetically sealed within an elongated tubular cladding having portions of the cladding walls constructed of an acoustically conductive medium, without violating the integrity of the cladding comprising the steps of:

generating an acoustic signal exterior of the cladding;

transmitting the acoustic signal through an acoustically conductive portion of the cladding wall in the plenum region along a selected path within the gas medium sealed within the plenum in a direction across the longitudinal axis of the fuel element that continues through a second acoustically conductive portion of the cladding wall;

receiving the acoustic signal after it has traversed the selected path through the gas, exterior of the second portion of the cladding wall;

converting the received acoustic signal into a corresponding electrical output; and calibrating the electrical output against a standard to provide a direct measure of the pressure of the gas within the enclosure over a wide range of pressures.

2. The method of claim 1 wherein the generating step generates pulsed acoustic energy.

3. The method of claim 2 wherein the acoustic energy is generated substantially within the ultrasonic frequency range.

4. The method of claim 1 wherein the transmitting step shapes the acoustic signal wave fronts to correspond to the geometry of the cladding walls.

5. The method of claim 1 wherein the acoustic signal travels a substantially linear path from the transmitter, through the gas enclosure, to the receiver.

6. The method of claim 1 wherein the received acoustic signal is directly proportional to the pressure of gas within the cladding.

7. The method of claim 1 including the steps of acoustically damping the walls of the cladding adjacent the first and second portions.

8. The method of claim 7 wherein the damping step substantially dissipates acoustic energy traveling around the cladding walls.

* * * * *